United States Patent [19]

Falciani et al.

[11] 4,299,955

[45] Nov. 10, 1981

[54] PROCESS FOR PREPARING DERIVATIVES OF 7-AMINO-DESACETOXY CEPHALOSPORANIC ACID

[75] Inventors: Marco Falciani; Renato Broggi, both of Milan, Italy

[73] Assignee: Dobfar S.p.A., Milan, Italy

[21] Appl. No.: 132,761

[22] Filed: Mar. 24, 1980

[30] Foreign Application Priority Data

Dec. 7, 1979 [IT] Italy ............................. 27962 A/79

[51] Int. Cl.³ ........................................ C07D 501/20
[52] U.S. Cl. ..................................... 544/30; 424/246
[58] Field of Search ................. 544/30, 21; 424/246

[56] References Cited

U.S. PATENT DOCUMENTS

| | | | |
|---|---|---|---|
| 3,502,663 | 3/1970 | Barnes | 544/30 |
| 3,531,481 | 9/1970 | Pfeiffer | 544/30 |
| 3,985,741 | 10/1976 | Crast et al. | 544/30 |

FOREIGN PATENT DOCUMENTS

| | | |
|---|---|---|
| 853974 | 10/1977 | Belgium . |
| 1133 | 3/1979 | European Pat. Off. . |
| 7304227 | 5/1974 | Netherlands . |
| 1327270 | 8/1973 | United Kingdom . |

*Primary Examiner*—Nicholas S. Rizzo
*Attorney, Agent, or Firm*—Oblon, Fisher, Spivak, McClelland & Maier

[57] ABSTRACT

Process for preparing cephalexine monohydrate and cephadroxyl monohydrate, according to which a reaction is carried out of a mixed anhydride prepared from a Dane salt of phenylglycine or p-hydroxyphenyl-glycine with a chloroformiate, with an aqueous solution of 7-ADCA in a solvent selected from the group comprising dimethyl sulphoxide, dimethylacetamide, formamide, dimethylformamide and dioxane.

2 Claims, No Drawings

PROCESS FOR PREPARING DERIVATIVES OF 7-AMINO-DESACETOXY CEPHALOSPORANIC ACID

This invention relates to a process for preparing derivatives of 7-amino-desacetoxy cephalosporanic acid having the formula

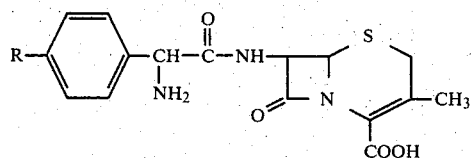

wherein R is —H or —OH.

The U.S. Pat. No. 3,985,741 describes the preparation of a compound of formula (I), wherein R is —OH (commonly referred to as "cephadroxyl"), according to which 7-amino-desacetoxy-cephalosporanic acid (commonly referred to as 7-ADCA) is reacted with a mixed anhydride provided by reacting p-hydroxy-phenylglycine Dane salt methylsodium with ethyl-chloroformiate in the presence of N-methylmorpholine. According to such a method very low yields are obtained, of no industrial interest, and with a product of low purity, as recognized by the assigner of such a patent in his successive Belgian Pat. No. 853,974 (at page 2).

This Belgian Pat. No. 853,974 also describes a process for producing cephadroxyl, according to which silicic ester of 7-ADCA is reacted with p-hydroxy-phenylglycine chloride-chlorohydrate emidioxan solvate in the presence of dimethylaniline as acceptor of hydrochloric acid: while having good yields, this method suffers from the disadvantage of providing a final compound having, as impurities, dimethylaniline and organic derivatives of silicon, such as hexamethyldisiloxane. Moreover, the use of chloride chlorohydrate of p-hydroxy-phenylglycine has the disadvantage of resulting in the building up of polymer materials, as impurities, which may give allergological characteristics to the product because of being the primary cause of the arising of allergic phenomena during the use in therapy on human beings.

The European Patent Application No. 1133 describes a process for producing cephadroxy, according to which a mixed anhydride, provided by reacting p-hydroxy-phenylglycine Dane salt methyl potassium with methyl chloroformiate in the presence of N-methylmorpholine and in a mixture of solvents comprising methylene chloride or methylisobutyl ketone and other cosolvents, is reacted with silicic esters of 7-ADCA.

Cephadroxyl obtained by this method has impurities resulting from the use of xylilderivative of 7-ADCA (such as hexamethyldisiloxane), which are highly difficult to remove due to insolubility thereof in water: moreover, the resort to the techniques of silanes constitutes a substantial heavy item on the costs of production.

The compound of formula (I) wherein R is —H (commonly referred to as cephalexine) is per se well known and known are a series of many patents describing the preparation thereof, among which the following U.S. patents can be mentioned: U.S. Pat. Nos. 3,507,861; 3,671,449; 3,634,416 and 3,676,437.

According to the present invention, for the preparation of derivatives of 7-amino-desacetoxy cephalosporanic acid having the formula

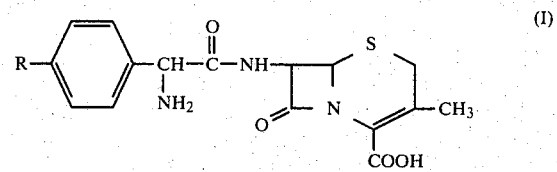

a mixed anhydride having the formula

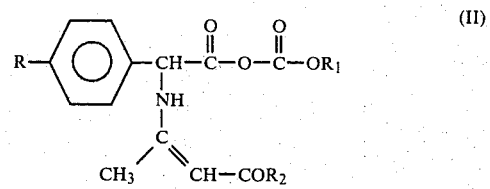

wherein R is —H or —OH; $R_1$ is methyl, ethyl or isobutyl; and $R_2$ is methoxyl or ethoxyl, is added at a temperature in the range of $-60°$ C. to $-10°$ C. to a solution obtained by dissolving 7-ADCA with triethylamine in an amount of 1.05–1.25 moles relative to 7-ADCA in a solvent selected from the group comprising dimethyl sulphoxide, dimethylacetamide, formamide, dimethylformamide and dioxane, in the presence of water and at a temperature in the range of 0° C. to 20° C., the mixed anhydride being at least in equimolar amount relative to 7-ADCA, then removing the enaminic group by lowering the pH of the reaction mixture to 0.8–2.5 by the addition of an aqueous solution of an inorganic acid, and finally isolating the finished product according to known techniques.

Preferably, the mixed anhydride of formula (II) is obtained by reacting the respective Dane salts, wherein R is —H or —OH and $R_2$ is methoxyl, with a chloroformiate (preferably ethyl chloroformiate) in acetone, in the presence of N-methylmorpholine, at a temperature in the range of $-60°$ C.—$-20°$ C., for example as described in U.S. Pat. No. 3,985,741.

Still preferably, the solvents per 7-ADCA are in an amount of about 10–25 moles for mole of 7-ADCA.

The mixed anhydride of formula (II) is a per se well known compound described, for example, in U.S. Pat. No. 3,985,741 and British Pat. No. 1,327,270.

For the preparation of the compounds of formula (I), attempts were made for reacting 7-ADCA in aqueous solution with anhydride of formula (II) in acetone or in a mixture of acetone and solvents used according to the present invention, but in both cases it was found that the yields in the final product are very low and of no industrial interest. Surprisingly, it was found that by dissolving 7-ADCA in an aqueous mixture of one of the above mentioned solvents and then adding such a solution to the solution of the mixed anhydride of formula (II), the yields in the final product are very high and of great industrial interest. Surprisingly, it was also found that the amount of triethylamine (in the range of 1.05–1.25 moles relative to 7-ADCA) used in the reaction is critical, since out of the specified range the yields in the final product are drastically reduced.

In the case of compounds of formula (I), wherein R is —OH, a filtering operation is required in the above mentioned U.S. Pat. No. 3,985,741 at the end of the synthesis reaction in order to remove the unreacted 7-ADCA, thereby providing the low yield afforded by the process of such a patent and the resulting requirement of purifying the finished product due to its poor purity. Unlike this case, in a process according to the present invention the compound 7-ADCA completely reacts with the result of obtaining a final product of high purity and yields. Finally, it may be pointed out that all of the reactants used in the process according to the present invention are of low cost, unlike in known techniques, where highly expensive reactants are used, such as the sililanting agents described in the European Pat. No. 1133 and said sililanting agents and p-hydroxy phenylglycine chloride chlorohydrate described in the Belgian Pat. No. 853,974.

For the production of compounds of formula (I), wherein R is —H, according to known processes (such as those described in the U.S. Pat. Nos. 3,507,861; 3,671,449; 3,634,416 and 3,676,437), a final product of poor purity is obtained due to the necessity of removing protective groups of 7-ADCA (such as 2,2,2-trichloroethyl, p-nitrobenzyl or trimethylsilil).

The use of sililanting agents enabling the removal of the protection and the use of D(—) phenylglycine chloride chlorohydrate is described, for example, in the Dutch Pat. No. 7,304,227.

On the other hand, use is made in the British Pat. No. 1,327,270 and in U.S. Pat. No. 3,694,437 of the techniques of Dane salts, and accordingly of mixed anhydrides.

This last mentioned patent associates the techniques of Dane salts with the use of sililanting agents protecting the compound 7-ADCA.

In order that the characteristics of the process according to the present invention be more clearly understood, some unrestrictive exemplary embodiment thereof will now be described.

EXAMPLE 1

(a) Preparation of ethoxy carbonyl D-α-1-carbomethoxy-propenyl)-amino p-hydroxy phenyl acetate A 2 l reaction flask was added with 250 ml anhydrous acetone, then cooled to —40° C. and added with 45.5 g (0.15 moles) potassium methyl Dane salt of D(—)-p-hydroxy phenylglycine; still at —40° C. under stirring 16.7 g (0.1545 moles) ethyl chloroformiate and 0.4 ml N-methyl morpholine were added. The exothermia was within —35° C. and the reaction was carried out at —35° C. for 2 hours. The reaction mixture was cooled to —55° C.

(b) Dissolution of 7-ADCA

In a 1 l reaction flask, 75 ml deionazed water and 32.1 g (0.15 moles) 7-amino desacetoxy cephalosporanic acid (7-ADCA) and 135 ml dimethyl sulphoxide were charged at —15° C., then adding 16.9 g (0.167 moles) triethylamine (TEA) in 15 minutes. 7-ADCA was dissolved (pH should not be higher than 10), then the solution thus obtained was cooled to 0° C.

(c) Cephadroxyl solvate of dimethyl formamide (DMF)

The suspension of mixed anhydride prepared in (a) and cooled to —55° C. was added with the solution of 7-ADCA prepared in (b). The exothermia was within —25° C. Then, the mixture was stirred at —25° C. for 1 hour. 1 ml reaction mixture was withdrawn and the following control was carried out: the mixture was diluted to 10 ml with H$_2$O, on GF 254 plate 30, 50, 100 ml were placed in comparison with a standard of 7-ADCA and a standard of cephadroxyl, and the eluition was carried out in 25 ml CH$_3$CN: 4 ml H$_2$O: 2 ml HCOOH. Detection was carried out with ninidrine observing the disappearance of 7-ADCA and the appearance of a spot of cephadroxyl. The temperature was raised to 0° C. and hydrolisis of enamine was initiated by adding a solution of 37% HCl to constant pH 1.8.

AT constant pH 1.8, 260 ml methylene chloride were added, stirring for 10 minutes, then decanting; the lower phase containing methylene chloride and acetone was discarded, whereas the upper phase containing cephadroxyl analyzed by HPCL reveals a conversion of 97% over theoric. The rich wates thus obtained were added with 250 ml dimethyl formamide (DMF) and 100 ml acetone and at 0° C. triethylamine was dropwise added to pH 6.5; then crystallization was primed or seeded with 0.5 g cephadroxyl solvate of DMF, obtaining a crystalline product that after 2 hours at 0° C. was filtered, washed on filter with a mixture of 100 ml DMF and H$_2$O (1:1), then with 100 ml acetone. The product obtained was dried at 40° C.

58.8 g cephadroxyl DMF solvate were obtained, equal to 90% on theoric. TLC single spot $[\alpha]_D = +122°$ on dry base, K.F. = 1.8% DMF (with GLC) = 16.2%.

(d) Preparation of cephadroxyl monohydrate

The solvate obtained in (c) was added with 100 ml H$_2$O stirred at 40° C. After 30 minutes at 40° C., the mixture was cooled to 0° C. and after 2 hours in crystallization filtered, washed with 30 ml ice water, dried at 40° C., and 41.5 g cephadroxyl monohydrate was obtained. K.F. = 5.8%; $[\alpha]_D = +168°$ on dry base, microbiological titer 933 mcg/mg.

The filtering mother liquors were diluted with 250 ml DMF; the product was crystallized and filtered. 3.6 g cephadroxyl DMF solvate was obtained which, upon conversion as above yield 2.5 g cephadroxyl monohydrate with $[\alpha]_D = +165°$ on dry base which, together with 41.5 previously obtained provide 45 g equal to a yield of 78.7% on the starting 7-ADCA.

EXAMPLE 2

(a) Preparation of ethoxy carbonyl D-α-(1-carbomethoxy-propenyl)amino p-hydroxy phenyl acetate 280 ml anhydrous acetone were introduced into a reaction flask, and after cooling to —45° C., 47.6 g (0.157 moles) D(—)p-hydroxy phenylglycine Dane salt potassium methyl were added; still at —45° C., 17.57 g (0.162 moles) ethyl chloroformiate and 0.4 ml N-methyl morpholine were added.

The exothermia was within —30° C., and the reaction was carried out at —30° C. for 2 hours. The reaction mixture was cooled to —50° C.

(b) Dissolution of 7-ADCA

The same process was followed and the same amounts of reactants were used as described in (b) of Example 1, with the exception of using 130 ml formamide instead of DMSO.

(c) Cephadroxyl solvate of DMF

The same process and amounts of reactants described in (c) of Example 1 were used.

The solution of rich waters was analyzed by HPLC with a conversion of 97%. 59.5 g cephadroxyl DMF solvate were isolated, with a yield of 90.9%. $[\alpha]_D = +122°$; K.F.=2%.

(d) Preparation of cephadroxyl monohydrate

Following the same procedure and using the same amounts described in (d) of Example 1, a total amount of 45.5 g cephadroxyl were obtained, microbiological titer 928 mcg/mg; $[\alpha]_D = +173°$ on dry base, with a yield of 79.6%.

EXAMPLE 3

The same procedure and amounts described in Example 1 were used, with the exception in step (b) of using 120 ml dimethyl formamide (DMF) instead of DMSO. 44 g cephadroxyl monohydrate were obtained; $[\alpha]_D = +170°$ on dry base; K.F.=5.8%; microbiological titer 932 mcg/mg.

EXAMPLE 4

(a) Preparation of ethoxy carbonyl D-α-(1-carbomethoxy-propenyl)amino p-hydroxy phenyl acetate The same amounts and process described in (a) of Example 1 were used.

The suspension of mixed anhydride was cooled to −45° C.

(b) Dissolution of 7-ADCA

The same process and amounts described in (b) of Example 1 were used, with the exception of using 130 ml dimethyl acetamide instead of DMSO.

(c) Preparation of cephadroxyl monohydrate

The solution of 7-ADCA prepared in (b) was added to the suspension of mixed anhydride prepared in (a) cooled to −45° C. The exothermia was within −25° C. The reaction was then carried out at −25° C. for 1 hour, on a portion of solution showing the formation of cephadroxyl and absence of starting 7-ADCA.

The temperature was then raised to 0° C. and hydrolisis of enamine was initiated by adding a solution of 37% HCl to constant pH 2.0 (still at 0° C.).

At constant pH 2.0, 260 ml methylene chloride were added, then stirring for 10 minutes and decanting. The lower phase containing methylene chloride plus acetone was discarded, whereas the upper phase containing cephadroxyl was analyzed by HPLC; a conversion of 95% on theoric was found.

The aqueous phases thus obtained were filtered on dicalite at +25° C. pH was brought to 5 with triethylamine; crystallization was seeded with 0.5 g cephadroxyl monohydrate and after 2 hours stirring it was filtered, and 23 g cephadroxyl monohydrate were obtained; $[\alpha]_D = +172°$; on dry base; K.F.=6.2%; microbiological titer 929 mcg/mg; yield 40.2%.

The filtering mother liquors were added with 300 ml DMF; cephadroxyl dimethyl formamide solvate was crystallized and collected by filtering and dried, obtaining 32.5 g dimethyl formamide solvate; $[\alpha]_D = +121°$; K.F.=1.8%. By conversion following the procedure described in (d) of Example 1, 22.9 g cephadroxyl monohydrate were obtained; $[\alpha]_D = +173°$; K.F=5.8%, microbiological titer 928 mcg/mg. The total yield was 45.9 g, that is 80.3% over theoric.

EXAMPLE 5

The same procedure was followed and the same amounts of reactants described in Example 1 were used, except that in step (b) 18.75 g (0.185 moles) triethylamine were used for the dissolution of 7-ADCA.

44 g cephadroxyl monohydrate were obtained; yield 76.9%; $[\alpha]_D = +171°$ on dry base; K.F.=6%; Titer HPLC 98.9% on dry base.

EXAMPLE 6

The same procedure was followed and the same amounts of reactants described in Example were used, except that in step (b) 16.2 g (0.160 moles) triethylamine were used for the dissolution of 7-ADCA.

44.5 g cephadroxyl monohydrate were obtained; yield 77.8%; microbiological titer 930 mcg/mg.

In accordance with the examples above described, cephadroxyl monohydrate was obtained as having the following average analytic characteristics:
Appearance: white crystalline powder
I.R.: positive indentification against standard
Moisture: 6.1%
pH 100 mg/ml: 4.5
Jiodometrical titer: 98.5% on dry material
Spectrophotometrica titer 260μ: 99.2% on dry material
H.P.L.C. titer: 99.8% on dry material
Specific rotation $[\alpha]_D$: +172° on dry material
Acidimetrical titer: 100.5% on dry material
Amino titer: 99% on dry material
Microbiological titer: 930 mcg/mg
Toxicity: not toxic
Stability at 65° for 7 days: 922 mcg/mg
Solvents determined for GLC:
 Dimethylaniline: not detectable
 Methylene chloride: 0.06%
 Triethylamine: 0.05%
 Acetone: 0.1%

EXAMPLE 7

(a) Preparation of ethoxy carbonyl D-α-(1-carbomethoxy propenyl)amino phenyl acetate A reaction flask was added with 250 ml anhydrous acetone, K.F. 0.1% and then with 43 g (0.15 moles) potassium methyl Dane salt of D(−)phenylglycine.

The mixture was cooled to −40° C., added with 16.7 g (0.1545 moles) ethyl chloroformiate and then with 0.3 ml N-methyl morpholine. The exothermia was within −30° C. The mixture was stirred at −30° C. for 2 hours.

The suspension of mixed anhydride was cooled to −50° C.

(b) Dissolution of 7-ADCA 80 ml deionized water were introduced into a reaction flask, followed by 32.1 g (0.15 moles) 7-ADCA and 130 ml DMSO. At 15° C. 16.9 g (0.167 moles) triethylamine were added with dissolution of 7-ADCA; the pH of the solution was controlled to 10, then the mixture was cooled to 0° C.

(c) Cephalexine monohydrate

The suspension of mixed anhydride prepared in (a) and cooled to −50° C. was rapidly added with the solution of 7-ADCA prepared in (b). The exothermia was within −30° C. The mixture was then stirred at −30° C. for 1 hour.

A portion of the solution was withdrawn and controlled with TLC (using as eluent 25 ml CH$_3$CN: 4 ml H$_2$O: 2 ml HCOOH). 1 ml solution was diluted to 10 ml with deionized water; 30, 50, 100 ml were placed on GF 254 plate with comparison of a standard of 7-ADCA and cephalexine, elution was carried out and detection with ninidrine. Formation of cephalexine and absence of 7-ADCA were observed.

The temperature was raised to 0° C., then hydrolysis was initiated of enamine through the addition of a solution of 37% hydrochloric acid to pH 1.8.

Upon hydrolysis completion and at constant pH 1.8, 200 ml methylene chloride were added, then stirring for 10 minutes and decanting for 30 minutes. The lower phase containing methylene chloride plus acetone was discarded, whereas on the upper phase containing the rich waters HPLC was carried out, showing a conversion of 97% in cephalexine monohydrate. The aqueous phase was then added with 50 ml methanol, heated to 30° C., pH adjusted to 4.3 with triethylamine causing the crystallization of the product, 200 ml acetone were added, the mixture was cooled to 15° C., and after stirring for 2 hours filtered, washed with 100 ml water:acetone 1:1, dried at 40° C.

45 g cephalexine monohydrate were obtained; K.F.=5.8%; $[\alpha]_D$=+156° on dry base; microbiological titer 928 mcg/mg, with a yield of 82% on 7-ADCA.

EXAMPLE 8

(a) Preparation of ethoxy carbonyl D-α-(1-carbomethoxy propenyl)amino phenyl acetate The same process and the same amounts of reactants described in (a) of Example 7 were used.

The suspension of mixed anhydride was cooled to −55° C.

(b) Dissolution of 7-ADCA

The same process and the same amounts of reactants described in (b) of Example 7 were used, with the exception of using 120 ml dimethyl formamide (DMF) instead of 130 ml DMSO.

(c) Cephalexine dimethyl formamide solvate

The suspension of mixed anhydride prepared in (a) and cooled to −55° C., was rapidly added with the solution of 7-ADCA prepared in (b). The exothermia was within −30° C., and the mixture was then reacted at −30° C. for 1 hour.

TLC was effected, showing the absence of unreacted 7-ADCA.

The temperature was raised to 0° C., then the hydrolysis of enamine was initiated by adding a solution of 37% hydrochloric acid to pH 2.2.

Upon hydrolysis completion at constant pH 2.2, 200 ml methylene chloride were added, then stirring for 10 minutes and decanting for 30 minutes. The lower phase containing methylene chloride plus acetone was discarded, whereas HPLC was effected on the upper phase containing the rich waters, showing a conversion of 96% in cephalexine monohydrate.

The aqueous phase was then added with 250 ml DMF and 100 ml acetone, the mixture was heated to +30° C. and the addition was started of triethylamine to pH 5. 0.5 g cephalexine DMF solvate were added and the product was crystallized. After 30 minutes, TEA was again added to pH 7, and after 2 hours at 30° C. the product was filtered, washed with a solution of 100 ml DMF:H$_2$O 9:1, then with acetone and finally dried at 40° C. 56.7 g cephalexine DMF solvate were obtained; K.F.=1.3%; $[\alpha]_D$=+110° on dry base. DMF (G.L.C.)=16%.

(d) Cephalexine monohydrate

The cephalexine DMF solvate as above obtained was added to 150 ml H$_2$O cooled to 0° C. at portions of 5 g each. Upon addition completion, 300 ml acetone were added and the mixture was allowed to crystallize at 0° C. for 3 hours.

The obtained product was filtered, washing with 200 ml of a mixture H$_2$O:acetone 1:1, then with acetone. The product was dried at 40° C., and 44.2 g cephalexine monohydrate were obtained, yield 80.7%, microbiological purity 928 mcg/mg. K.F.=5.5% $[\alpha]_D$=+155° on dry base.

EXAMPLE 9

(a) Preparation of ethoxy carbonyl D-α-(1-carbomethoxy propenyl)amino phenyl acetate 230 ml anhydrous acetone and 43 g (0.15 moles) potassium methyl Dane salt of D(−) phenyl glycine were added to a reaction flask. The mixture was cooled to −45° C., then adding 16.7 g (0.1545 moles) ethyl chloroformiate and 0.3 ml N-methyl morpholine. The exothermia was within −25° C. The mixture was stirred at −25° C. for 2 hours.

The suspension of mixed anhydride was cooled to −55° C.

(b) Dissolution of 7-ADCA 80 ml deionized water and then 32.1 g (0.15 moles) formamide were introduced into a reaction flask, 16.9 g (0.167 moles) triethylamine at 15° C. were added with dissolution of 7-ADCA in 15 minutes. The mixture was then cooled to 0° C.

(c) Cephalexine formamide solvate

The suspension of mixed anhydride prepared in (a) and cooled to −55° C. was rapidly added with the solution of 7-ADCA prepared in (b). The exothermia was within −25° C., and the mixture was allowed to react at −25° C. for 1 hour. TLC was effected, showing the absence of unreacted 7-ADCA.

The temperature was raised to 0° C., then the hydrolysis of enamine was initiated by adding a solution of 37% hydrochloric acid to pH 1.6.

Upon hydrolysis completion and at constant pH 1.6, HPLC was effected, showing a conversion of 97% on theoric.

The rich waters were filtered on dicalite, then heating to +30° C. and triethylamine were drpwise added to pH 5. The product was crystallized, allowed to rest at 30° C. for 1 hour, then cooled to 0° C. and after 2 hours at this temperature filtered, washed with acetone and then dried at 40° C.

53 g cephalexine formamide solvate were obtained; $[\alpha]_D$=+100° on dry base; K.F.=2.1%, formamide=10.5% (G.L.C).

(d) Cephalexine monohydrate

The formamide solvate above obtained was converted in cephalexine by following the same process as described in (d) of Example 8. 43.8 g were obtained, with a yield of 80% on 7-ADCA. $[\alpha]_D = +154°$ on dry base; microbiological titer 927 mcg/mg.

EXAMPLE 10

(a) Preparation of ethoxy carbonyl D-α-(1-carbomethoxy propenyl)amino phenyl acetate 250 ml anhydrous acetone K.F.=0.1% and 45.9 g (0.160 moles) potassium methyl Dane salt of D(−)phenylglycine were added to a reaction flask. The mixture was cooled to −40° C., then added with 17.9 g (0.165 moles) ethyl chloroformiate and 0.3 ml N-methyl morpholine. The exothermia was within −35° C. The mixture was then stirred at the temperature of −35° C. for 2 hours.

The suspension was cooled to −50° C.

(b) Dissolution of 7-ADCA 80 ml deionized water and then 32.1 g (0.15 moles) 7-ADCA and 135 ml dimethylacetamide (DMAC) were introduced into a reaction flask. At 15° C., 16.9 g (0.167 moles) triethylamine were added. 7-ADCA was dissolved, while controlling pH of the solution to about 10, then cooling to 0° C.

(c) Preparation of cephalexine monohydrate

The same process with the amounts of reactants described in (c) of Example 7 was followed.

43 g cephalexine monohydrate were obtained with a yield of 78.5%. K.F.=5.85%.

$[\alpha]_D = +155°$ on dry base; spectrophotometrical titer 98.8%.

EXAMPLE 11

(a) Preparation of ethoxy carbonyl D-α-(1-carbomethoxy propenyl)amino phenyl acetate 220 ml anhydrous acetone K.F.=0.1% and then 43 g (0.15 moles) potassium methyl Dane salt of D(−)-phenylglycine were added to a reaction flask. The mixture was cooled to −35° C. and 16.7 g (0.1545 moles) ethyl chloroformiate were added, then 0.4 ml N-methyl morpholine.

The exothermia was within −30° C. The mixture was stirred at −30° C. for 2 hours. The suspension of mixed anhydride was cooled to −55° C.

(b) Dissolution of 7-ADCA 80 ml deionized water and then 32.1 g (0.15 moles) 7-ADCA and 130 ml DMSO were introduced into a reaction flask. At 15° C., 18.75 g (0.185 moles) triethylamine were added with dissolution of 7-ADCA and after stirring for 30 minutes, the solution was cooled to 0° C.

(c) Cephalexine monohydrate

By following the same process and using the same amounts of reactants described in (c) of Example 7, 43.5 g cephalexine monohydrate were obtained, yield 79.4%. Microbiological titer 928 mcg/mg. K.F.=6.3%.

EXAMPLE 12

(a) Preparation of ethoxy carbonyl D-α-(1-carbomethoxy propenyl)amino phenyl acetate The same process was followed with the amounts of reactants described in (a) of Example 11. The suspension of mixed anhydride was cooled to −50° C.

(b) Dissolution of 7-ADCA 85 ml deionized water and then 32.1 g (0.15 moles) 7-ADCA and 135 ml dimethylacetamide were introduced into a reaction flask. At 15° C., the addition of 16.2 g (0.160 moles) triethylamine was started. The addition ended in 10 minutes, with pH at about 10 and complete dissolution of 7-ADCA. The solution obtained was cooled to 0° C.

(c) Cephalexine monohydrate

The same process with the amounts of reactants described in (c) of Example 7 was used.

44.2 g cephalexine monohydrate were obtained, yield 80.7%. $[\alpha]_D = +155°$ on dry base. K.F.=6.5%.

In all of the above described examples the solvents were used for dissolving 7-ADCA. If, rather than being used for dissolution of 7-ADCA, the solvents would be used for the dissolution of mixed anhydride during the preparation thereof, a very high reduction in yields of the final product would be provided, while following the same procedures as described.

In accordance with the examples above described, cephalexine monohydrate is obtained as having the following characteristics of analytic nature:
Appearance: white crystalline powder
I.R.: positive identification against standard
Moisture KF: 6.1%
pH 100 mg/ml: 4.2
Jiodometrical titer: 99.2% on anhydrous material
Spectrophotometrical titer: 98.8% on anhydrous material
HPLC titer: 98.5% on anhydrous material
Acidimetrical titer: 100.8% on anhydrous material
Amino titer: 99.2% on anhydrous material
Specific rotation $[\alpha]_D$: +155° on anhydrous material
Microbiological titer: 932 mcg/mg
Toxicity: not toxic
Stability 65° for 7 days: 920 mcg/mg
Determined solvents for GLC:
Dimethylaniline: not detectable
Methylene chloride: 0.04%
Triethylamine: 0.05%
Acetone: 0.1%.

What we claim is:

1. A process for preparing derivatives of 7-amino-desacetoxy cephalosporanic acid having the formula

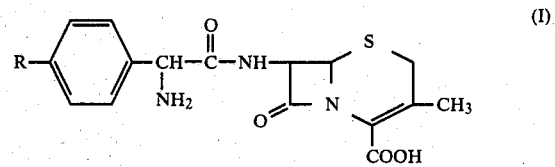

(I)

wherein R is —H or —OH, wherein a mixed anhydride having the formula

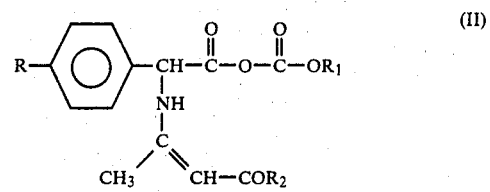

(II)

wherein R is —H or —OH, $R_1$ is methyl, ethyl or isobutyl, and $R_2$ is methoxyl or ethoxyl, is added at a temperature in the range of $-60°$ C. to $-10°$ C. to a solution obtained by dissolving 7-ADCA with excess triethylamine, in an amount in the range of 1.05–1.25 moles over 7-ADCA, in a solvent selected from the group consisting of dimethyl sulphoxide, dimethylacetamide, formamide, dimethylformamide and dioxane, in the presence of water and at a temperature ranging between $0°$ C. and $+20°$ C., the mixed anhydride being in an amount at least equimolar with respect to the amount of 7-ADCA, then removing the enamine group by lowering the pH of the reaction mixture to 0.8–2.5 by adding an aqueous solution of an inorganic acid, and finally isolating said derivative product.

2. A process according to claim 1, wherein the solvents of 7-ADCA are in an amount ranging between about 10 and 25 moles per mole of 7-ADCA.

* * * * *